(12) United States Patent
Han et al.

(10) Patent No.: US 9,970,753 B2
(45) Date of Patent: May 15, 2018

(54) SYSTEM AND METHOD OF MEASURING GEOMETRIC CHARACTERISTICS OF OBJECT

(71) Applicant: General Electric Company, Schenectady, NY (US)

(72) Inventors: Xu Han, Shanghai (CN); Guangping Xie, ShangHai (CN); Kevin George Harding, Niskayuna, NY (US); John Brandon Laflen, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 233 days.

(21) Appl. No.: 14/863,481

(22) Filed: Sep. 24, 2015

(65) Prior Publication Data

US 2016/0084644 A1    Mar. 24, 2016

(30) Foreign Application Priority Data

Sep. 24, 2014    (CN) .......................... 2014 1 0493810

(51) Int. Cl.
*G01B 11/14* (2006.01)
*G01B 11/30* (2006.01)
(Continued)

(52) U.S. Cl.
CPC ............ *G01B 11/303* (2013.01); *G01B 11/02* (2013.01); *G01B 11/24* (2013.01); *G01N 21/84* (2013.01); *G06T 7/60* (2013.01)

(58) Field of Classification Search
CPC ......... G01B 11/14; G01B 11/24; G01B 11/02; G01B 11/30; G01B 11/303;
(Continued)

(56) References Cited

U.S. PATENT DOCUMENTS 4,411,528 A  * 10/1983  Newcomb ............. G01B 11/00
                                                         356/394
5,325,177 A     6/1994  Peterson
(Continued)

FOREIGN PATENT DOCUMENTS

CN          1888817 A      1/2007
CN        203657757 U      6/2014
(Continued)

OTHER PUBLICATIONS

Jun et al., "A study on a detection system based on ring laser used for inner wall of deep hole", Opto-Electronic Engineering, vol. No. 31, Issue No. 1, pp. 32-35, Jan. 2004.
(Continued)

*Primary Examiner* — Tri T Ton
(74) *Attorney, Agent, or Firm* — Peter T. DiMauro; GE Global Patent Operation

(57) ABSTRACT

A system includes a light emitting unit, a front mirror, a rear mirror, an imaging unit and a processor. The light emitting unit is configured to emit a collimated light beam. The front mirror is configured to reflect part of the collimated light beam to produce and project a front focused ring of structured light to an object to obtain a front reflected ring of light, and configured to allow part of the collimated light beam to pass by. The rear mirror is positioned downstream of a light transmitting path of the front mirror. The rear mirror is configured to reflect at least part of the collimated light beam passing by the front mirror to produce and project a rear focused ring of the structured light to the object to obtain a rear reflected ring of light.

20 Claims, 10 Drawing Sheets

(51) Int. Cl.
*G06T 7/60* (2017.01)
*G01B 11/02* (2006.01)
*G01B 11/24* (2006.01)
*G01N 21/84* (2006.01)

(58) Field of Classification Search
CPC ...... G01B 9/02019; G01N 21/84; G06T 7/60; G06T 2207/10004; G06T 7/0004
USPC .................................................. 356/600–640
See application file for complete search history.

(56) References Cited

U.S. PATENT DOCUMENTS

| | | | |
|---|---|---|---|
| 5,933,231 | A | 8/1999 | Bieman et al. |
| 7,903,245 | B2 | 3/2011 | Miousset et al. |
| 2004/0075842 | A1 | 4/2004 | Dunn et al. |
| 2008/0259346 | A1 | 10/2008 | Strahle |
| 2010/0073935 | A1* | 3/2010 | Ben-Ezer ........... G01N 21/8806 362/311.12 |
| 2012/0224189 | A1 | 9/2012 | Kessler |
| 2013/0229667 | A1 | 9/2013 | Goeing et al. |
| 2014/0211212 | A1 | 7/2014 | Yokota |

FOREIGN PATENT DOCUMENTS

| | | |
|---|---|---|
| CN | 103968777 A | 8/2014 |
| JP | 2009025006 A | 2/2009 |

OTHER PUBLICATIONS

Wakayama et al., "Development of a compact inner profile measuring instrument", Two- and Three-Dimensional Methods for Inspection and Metrology V, Proc. of SPIE, vol. No. 6762, pp. 67620D-1-67620D-5, Oct. 10, 2007.

Wakayama et al., "Measurement of inner and/or outer profiles of pipes using ring beam devices", International Conference on Optical Instruments and Technology: Optoelectronic Imaging and Process Technology, Proc. of SPIE, vol. No. 7513, pp. 751306-1-751306-8, Nov. 24, 2009.

Yoshizawa et al., "Development of an inner profile measurement instrument using a ring beam device", Optical Metrology and Inspection for Industrial Applications, Proc. of SPIE, vol. No. 7855, pp. 78550B-1-78550B-8, Nov. 11, 2010.

Shen et al., "A Multifunctional and Portable Optical Sensor for Quantitative Characterization of 3D Surface Texture Properties", International Journal of Information Acquisition, vol. No. 7, Issue No. 4, pp. 269-284, Dec. 2010.

Han et al., "Development of feature extraction analysis for a multi-functional optical profiling device applied to field engineering applications", Dimensional Optical Metrology and Inspection for Practical Applications IV, Proc. of SPIE, vol. No. 9489, pp. 948907-1-948907-8, May 14, 2015.

European Search Report and Opinion issued in connection with corresponding EP Application No. 15186566.4 dated Feb. 15, 2016.

Unofficial English Translation of Chinese Office Action issued in connection with corresponding CN Application No. 201410493810.5 dated Aug. 17, 2017.

* cited by examiner

SYSTEM AND METHOD OF MEASURING GEOMETRIC CHARACTERISTICS OF OBJECT

BACKGROUND

Embodiments of the disclosure relate generally to systems and a method of measuring, and more particularly to systems and a method of measuring geometric characteristics of object.

The measurement of geometric characteristics of an object, such as an inner surface of a cavity, a flat or curved open surface, a gap between two edges, a radius between two intersecting surfaces or a step between two surfaces, has always been a challenge. One conventional measurement system that measures the geometric properties of the object includes a light source emitting a light beam to a mirror, such as an axicon. The mirror reflects the light beam into a focused ring of light to the surface of the object to obtain a reflected ring of light. The measurement system obtains the geometric characteristics of the object according to the reflected ring of light. However, measuring geometric characteristics with one focused ring of light has its limitations. For example, only one profile of a cross-section of the object can be obtained. Furthermore, when a plane of the focused ring is at an angle that is not orthogonal with the surface of the object, the geometric characteristics are not correctly extracted.

It is desirable to provide a solution to address at least one of the above-mentioned problems.

BRIEF DESCRIPTION

In accordance with one embodiment disclosed herein, a measurement system is provided. The system includes a light emitting unit, a front mirror, a rear mirror, an imaging unit and a processor. The light emitting unit is configured to emit a collimated light beam. The front mirror is configured to reflect part of the collimated light beam to produce and project a front focused ring of structured light to an object to obtain a front reflected ring of light, and configured to allow part of the collimated light beam to pass by. The rear mirror is positioned downstream of a light transmitting path of the front mirror. The rear mirror is configured to reflect at least part of the collimated light beam passing by the front mirror to produce and project a rear focused ring of the structured light to the object to obtain a rear reflected ring of light. The imaging unit is configured to record an integrated image of the front reflected ring and the rear reflected ring. The processor is coupled to the imaging unit and configured to obtain at least one geometric characteristic of the object according to the integrated image from the imaging unit.

In accordance with another embodiment disclosed herein, a system is provided. The system includes a light emitting unit, a light structuring device, an imaging unit and a processor. The light emitting unit is configured to emit a collimated light beam. The light structuring device is configured to generate structured light. The light structuring device includes a front conical reflecting surface and a rear conical reflecting surface. The front conical reflecting surface is configured to reflect part of the collimated light beam into a front focused ring of the structured light to obtain a front reflected ring of light, and allow part of the collimated light beam to pass by. The rear conical reflecting surface is configured to reflect at least part of the collimated light beam passing by the front conical reflecting surface into a rear focused ring of the structured light to obtain a rear reflected ring of light. The imaging unit is configured to record an integrated image of the front reflected ring and the rear reflected ring. The processor is coupled to the imaging unit and configured to obtain the at least one geometric characteristic of the cavity according to the image from the imaging unit.

In accordance with another embodiment disclosed herein, a method is provided. The method includes emitting a collimated light beam. The method further includes reflecting part of the collimated light beam to produce and project a front focused ring of structured light to an object to obtain a front reflected ring of light and passing part of the collimated light beam. The method further includes reflecting at least part of the passed collimated light beam to produce and project a rear focused ring of the structured light to the object to obtain a rear reflected ring of light. The method further includes recording an integrated image of the front reflected ring of light and the rear reflected ring of light. The method includes obtaining at least one geometric characteristic of the object according to the integrated image.

BRIEF DESCRIPTION OF THE DRAWINGS

These and other features and aspects of the present invention will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a", "one" and "an" do not denote a limitation of quantity, but rather denote the presence of at least one of the referenced items. The use of "including," "comprising", "having" or "contain" and variations thereof herein are meant to encompass the items listed thereafter and equivalents thereof as well as additional items. Although the terms "connected" and "coupled" are often used to describe physical or mechanical connections or couplings, they are not intended to be so restricted and can include optical or electrical connections or couplings, whether direct or indirect.

Figure 1:
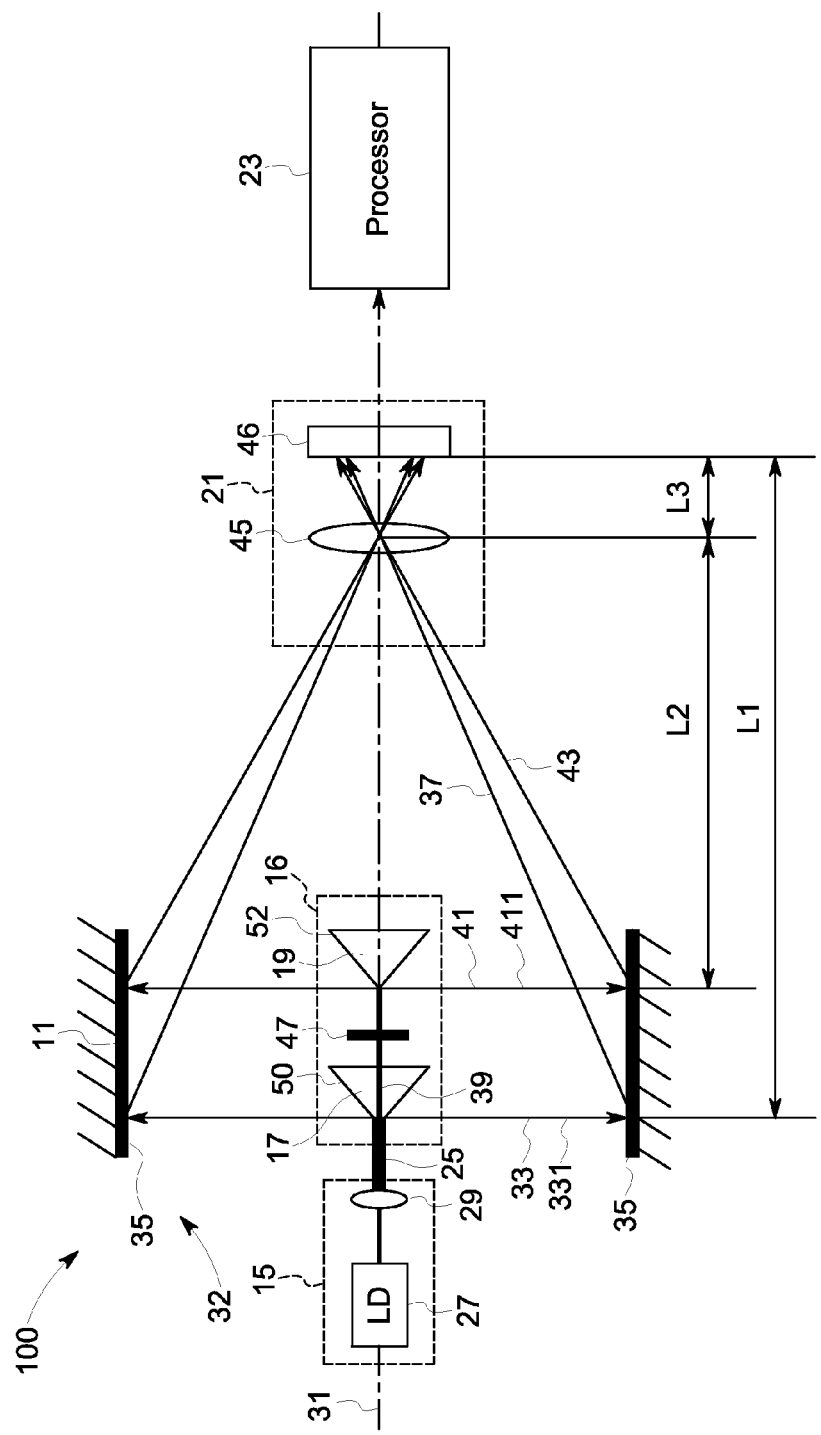
FIG. 1 is a schematic view of a measuring system in accordance with an embodiment.

FIG. 1 illustrates a schematic view of a measuring system 100 in accordance with an embodiment. The measuring system 100 can be used to measure at least one geometric characteristic of an object 11. For example, a three-dimensional profile of a cavity, a diameter of a cylindrical cavity, a transition radius of a curved open surface, a step feature of a step and a distance between two edges of a gap can be measured. Cracks and bumps on the surface can also be detected by the measuring system 100. The measuring system 100 includes a light emitting unit 15, a light structuring device 16, an imaging unit 21 and a processor 23. The light emitting unit 15 is configured to emit a collimated light beam 25. In one embodiment, the light emitting unit 15 includes a light source 27, such as laser diode, light emitting diode, or some other point light source, and collimating lens 29. The collimating lens 29 is configured to collimate light from the light source 27 to generate the collimated light beam 25. In another embodiment, the light emitting unit 15 includes multiple collimating lenses arranged to collimate the light from the light source 27. In yet another embodiment, the light emitting unit 15 includes one or two other optical components. For example, plane mirrors are employed to change a transmitting direction of the light from the light source 27 which is positioned away from a measuring axis 31 of the measuring system 100. In the illustrated embodiment, the light source 27 and the collimate lens 29 are arranged on the measuring axis 31. It should be understood that while the figures depict the light beams and reflections by a single lined arrow, the light is not a single beam but multiple beams. In this example, the object 11 is a pipe and the front reflected ring of light 37 and rear reflected ring of light 43 is for the interior of a section of the pipe.

The light structuring device 16 is configured to generate structured light 32 and includes a front mirror 17 and a rear mirror 19. The front mirror 17 is configured to reflect part of the collimated light beam 25 to produce and project a front focused ring 33 of the structured light 32 to a reflective surface 35 of the object 11 to obtain a front reflected ring of light 37, and configured to allow part of the collimated light beam 25 to pass by the front mirror, wherein the term pass by refers to light that passes through the light passing channel of the front mirror or around the front mirror. The front mirror 17 includes a front conical reflecting surface 50 that is configured to reflect part of the collimated light beam 25 into the front focused ring 33 of the structured light 32. In one example the front mirror 17 allows part of the collimated light beam 25 to pass by the front mirror 17.

In the illustrated embodiment, the front mirror 17 includes a light passing channel 39 therein allowing the collimated light beam 25 to pass by the front mirror 17. The light channel 39 extends through the front conical reflecting surface 50 from an apex thereof. A diameter of the light passing channel 39 is less than the diameter of the collimated light beam 25 so as to let part of the collimated light beam 25 pass through. In one embodiment, the light passing channel 39 is a through hole in the front mirror 17 extending along the measuring axis 31. In another embodiment, the light passing channel 39 is made from light-passing material, such as glass, to let the collimated light beam 25 pass through. In one example the front mirror 17 has a flat apex, that is to say, the light passing channel 39 is cylinder shaped with a flat end to make the collimated light beam 25 transmit along the measuring axis 31.

In the illustrated embodiment, the front conical reflecting surface 50 of the front mirror 17 reflects an outer circle of the collimated light beam 25 and passes the inner circle of the collimated light beam 25 therethrough to the rear mirror 19. As shown, in this example the front mirror 17 is arranged on the measuring axis 31. In the illustrated embodiment, the front mirror 17 includes a conical mirror, such as a 45 degree conical mirror, with the light passing channel 39 extending from the apex thereof and along a central axis thereof. The central axis of the front mirror 17 is aligned to the measuring axis 31. The front focused ring 33 is approximately perpendicular to the measuring axis 31. The front focused ring 33 is reflected from the inner reflective surface 35 to generate the front reflected ring of light 37.

The rear mirror 19 is positioned downstream of the light transmitting path of the front mirror 17. The rear mirror 19 is configured to reflect at least part of the collimated light beam 25 passing by the light passing channel 39 of front mirror 17 to produce and project a rear focused ring 41 of the structured light 32 to the reflective surface 35 of the object 11 to obtain a rear reflected ring of light 43. The rear mirror 19 includes a rear conical reflecting surface 52 configured to reflect at least part of the portion of the collimated light beam 25 passing by the light passing channel 39 into the rear focused ring 41.

In the illustrated embodiment, the structured light 32 is formed by the front focused ring 33 and the rear focused ring 41. The rear mirror 19, such as a conical mirror or a prism, is arranged on the measuring axis 31. In the illustrated embodiment, the rear mirror 19 is a 45 degree conical mirror. In one embodiment, the rear mirror 19 is coaxial with the front mirror 17, and the rear conical reflecting surface 52 is coaxial with the front conical reflecting surface 50. A front plane 331 of the front focused ring 33 of the structured light 32 is parallel to the rear plane 411 of the rear focused ring 41 of the structured light 32. The planes of the front focused ring 33 and the rear focused ring 41 are approximately perpendicular to the measuring axis 31. The rear focused ring 41 is reflected by the reflective surface 35 to generate the rear reflected ring 43.

The imaging unit 21, such as a camera, is configured to record an integrated image of the front reflected ring 37 and the rear reflected ring 43. The imaging unit 21 includes a lens or a lens set 45 and an area array detector 46. The front reflected ring of light 37 and the rear reflected ring of light 43 are adjusted by the lens 45. The image is recorded at the area array detector 46 such as CCD, CMOS. In one embodiment, the light emitting unit 15 and the imaging unit 21 are positioned on opposite sides of the front mirror 17 and the rear mirror 19.

The processor 23 is coupled to the imaging unit 21 and configured to obtain the geometric characteristic of the object 11 according to the image from the imaging unit 21. The processor 23, in one embodiment, is a computer or other computing devices such as field programmable gate arrays (FPGA), microprocessors, and the like, wherein the processor can be a multi-core processor. The processor 23 connects corresponding points on the front reflected ring 37 and the rear reflected ring 43 to obtain the geometric characteristic of the object 11. For example, the processor 23 generates a two-dimensional (2D) profile of a front cross-section from the front reflected ring 37 and a 2D profile of a rear cross-section from the rear reflected ring 43, and outputs a 3D profile of a cavity through linearly connecting the corresponding points of the profiles of the front cross-section and the profile of the rear cross-section. It should be noted that this example is merely illustrative and is non-limiting.

In one embodiment, the measuring system 100 further includes a shutter 47 being operative to stop producing the rear reflected ring of light 43 by stopping the collimated light beam 25 from reaching the rear mirror 19. The collimated light beam 25 that goes through the light passing channel 39 passes through the shutter 47 when the shutter 47 is opened, and is stopped when the shutter 47 is closed. In the illustrated embodiment, the shutter 47 is positioned in the light transmitting path between the front mirror 17 and the rear mirror 19. The shutter 47 is used to stop the collimated light beam 25 from reaching the rear mirror 19 so that only the front reflected ring of light 37 is generated and imaged without the rear reflected ring of light 43. In another embodiment, the shutter 47 is positioned around the rear mirror 19 to stop the rear focused ring of light 41 from reaching the object 11. In still another embodiment, the shutter 47 may be positioned to stop the rear reflected ring of light 43 from reaching the imaging unit 21.

In one example, the imaging unit 21 is configured to record an individual image of the front reflected ring of light 37, and the processor 23 is configured to separate the rear reflected ring 43 from the front reflected ring 37 in the integrated image by using the individual image of the front reflected ring of light 37. The shutter 47 may include, for example, a mechanical shutter, a liquid crystal shutter or any other devices capable of switching between a light-passing condition and a light-stopping condition.

Figure 2:
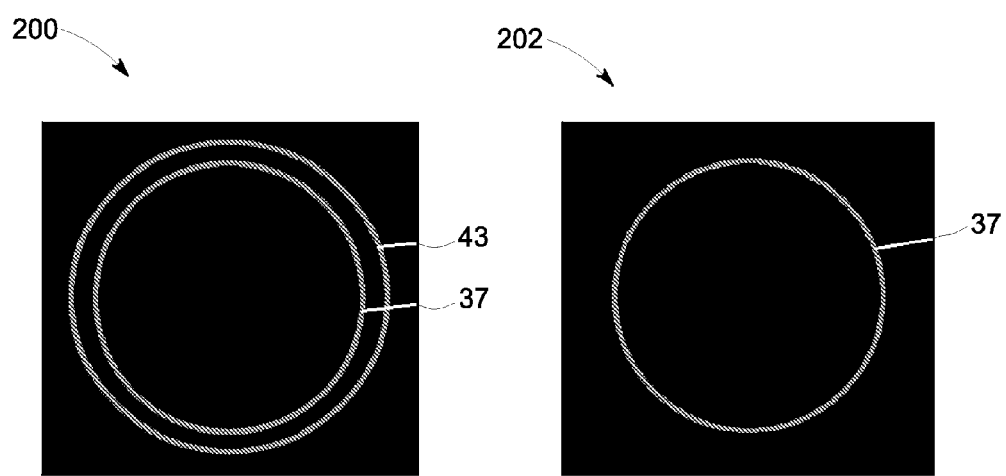
FIG. 2 is a schematic view of an integrated image and an individual image in accordance with an embodiment.

FIG. 2 illustrates a schematic view of the integrated image 200 and the individual image 202 in accordance with an embodiment. The integrated image 200 shows the image of the front reflected ring of light 37 and the image of the rear reflected ring of light 43. The image of the front reflected ring 37 shows a profile of the front cross-section of the reflected surface 35 of the object 11, and the image of the rear reflected ring 43 shows a profile of the rear cross-section of the reflected surface 35. In the illustrated embodiment, the images of the front reflected ring 37 and the rear reflected ring 43 are both annular, that is to say the front cross-section and the rear cross-section of the reflected surface 35 are both circular such as from an interior of a pipe. It should be noted that this example is merely illustrative and is non-limiting. The images of the front reflected ring 37 and the rear reflected ring 43 are changed according to the profile of the reflected surface 35 in particular applications.

The individual image 202 only shows the image of the front reflected ring of light 37. The rear reflected ring 43 and the front reflected ring 37 can be separated according to the integrated image 200 and the individual image 202. Accordingly, points on the rear reflected ring 43 and the front reflected ring 37 in the integrated image 200 can be distinguished even if the points on the rear reflected 43 and the points on the front reflected 37 are close to each other or overlap in the integrated image 200. With the reference to FIG. 1, the image of the front reflected ring of light 37 can be amplified by being multiplied by an amplifying coefficient which is a result of a distance L1 between the front focused ring of light 33 and the lens 45 divided by a distance L3 between the lens 45 and the area array detector 46 to obtain an image of the front focused ring of light 33. Similarly, the image of the rear reflected ring of light 43 can be amplified by being multiplied by another amplifying coefficient which is a result of a distance L2 between the rear focused ring of the light 41 and the lens 45 and the distance L3 to obtain an image of the rear focused ring of light 41. In this embodiment, the images of the front focused ring 33 and the rear focused ring 41 are circles overlapping with each other.

Figure 3:
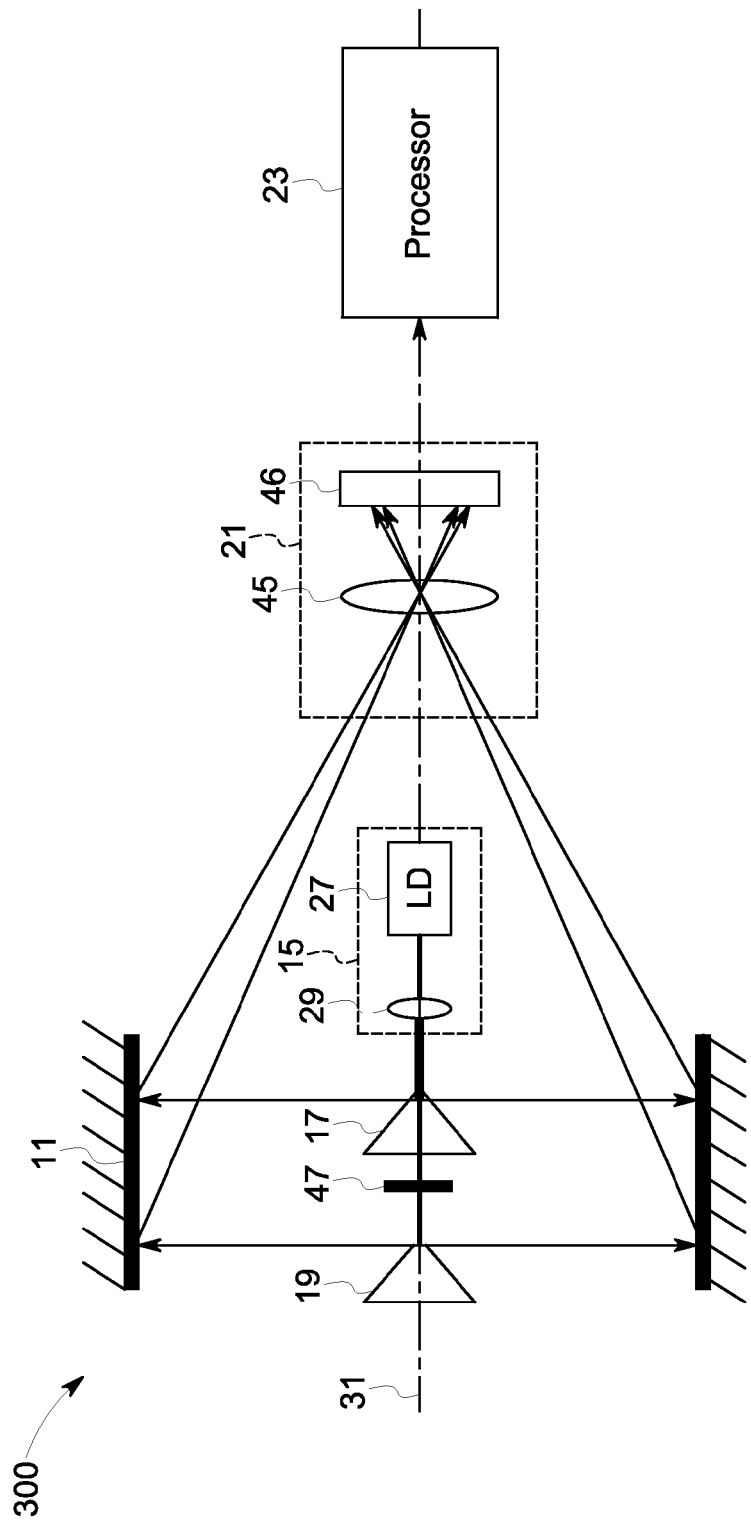
FIG. 3 is a schematic view of the measuring system in accordance with another embodiment.

FIG. 3 illustrates a schematic view of a measuring system 300 in accordance with another embodiment. The measuring system 300 in FIG. 3 is similar to the measuring system 100 in FIG. 1. Compared with the measuring system 100 in FIG. 1, in FIG. 3, the light emitting unit 15 and the imaging unit 21 of the measuring system 300 are positioned on the same side of the front mirror 17 and the rear mirror 19 so that the structure of the measuring system is compact. The light emitting unit 15 emits the collimated light beam 25 from the light source 27 through the collimating lens 29 and onto the front mirror 17 that reflects some light to the surface 35 of the object 11 and some light passes by the front mirror to the shutter 47 and onto the rear mirror 19. The rest of the processing is the same.

Figure 4:
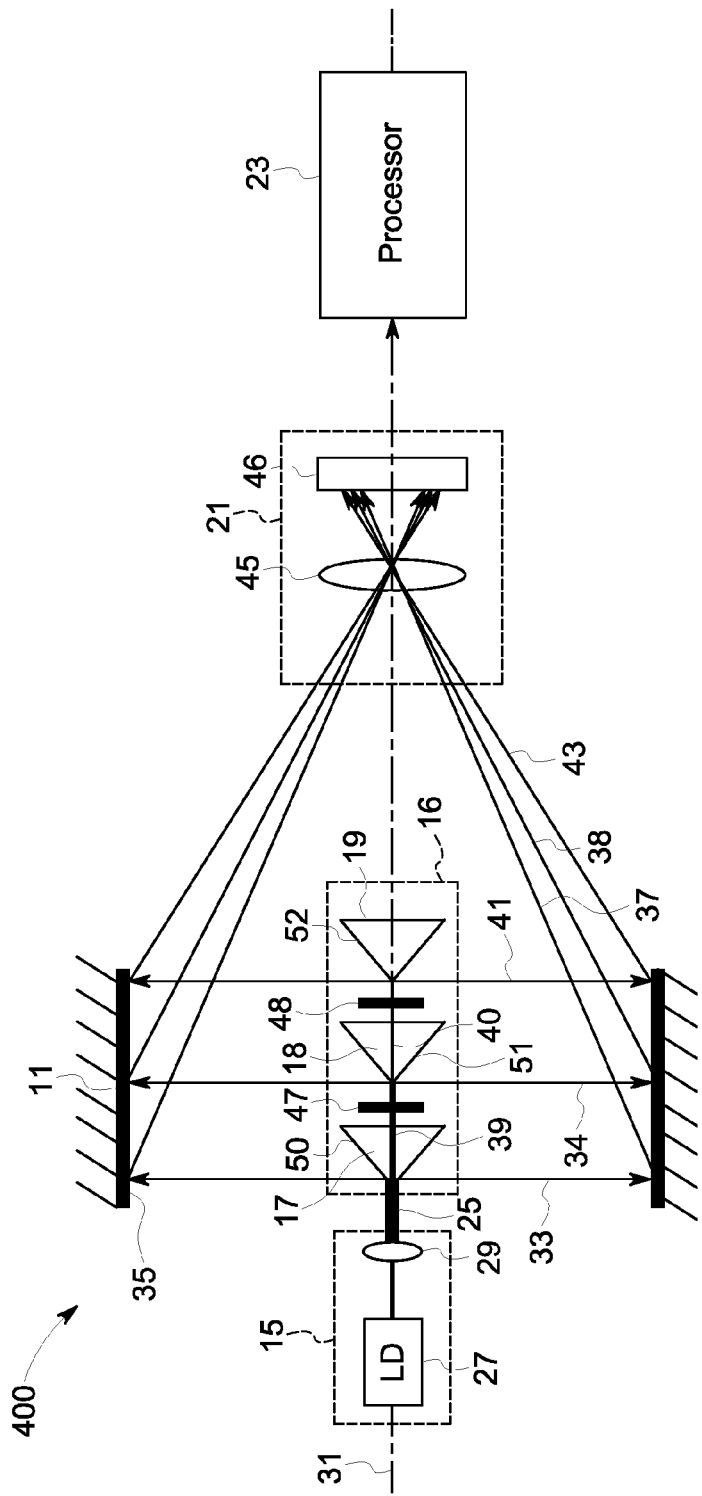
FIG. 4 is a schematic view of the measuring system in accordance with another embodiment.

FIG. 4 illustrates a schematic view of a measuring system 400 in accordance with another embodiment. The measuring system 400 in FIG. 4 is similar to the measuring system 100 in FIG. 1. Compared with the measuring system 100 in FIG. 1, the light structuring device 16 further includes at least one middle mirror 18 positioned in the light transmitting path between the front mirror 17 and the rear mirror 19. The at least one middle mirror 18 is configured to reflect part of the collimated light beam 25 to produce and project at least one middle focused ring 34 of the structured light 32 to the object 11 to obtain at least one middle reflected ring of light 38, and configured to pass part of the collimated light beam 25 to the rear mirror 19. The middle mirror 18 includes a middle conical reflecting surface 51 configured to reflect part of the collimated light beam 25 into the middle focused ring 34 from part of the structured light 32 and pass by part of the collimated light beam 25. For illustration purpose only, one middle mirror 18 is illustrated. The light structuring device 16 may include any number of the middle mirrors 18. The additional mirror(s) 18 can be used in certain applications where the imaging requires greater accuracy such that the spacing between the rings 33, 34, 41 is smaller and allows for greater resolution. Alternatively, the additional mirror(s) 18 can allow for a greater area for the surface 35 of the object 11 to be captured thereby increasing the speed of processing of the object 11.

In the illustrated embodiment, the middle mirror 18 includes a light passing channel 40 which is similar to the light passing channel 39 in the front mirror 17. A diameter of the light passing channel 40 is less than that of the light passing channel 39 of the front mirror 17. In one embodiment, the light structuring device 16 includes two or more middle mirrors 18. The diameter of the light passing channel of a downstream middle mirror 18 is less than that of the light passing channel of an upstream middle mirror 18. Accordingly, the collimated light beam 25 is reflected by the middle mirrors 18 and passes through the middle mirrors 18.

The middle reflected ring 34 is also imaged by the imaging unit 21 and processed to obtain the geometric characteristic of the object 11 together with the front reflected ring 37 and the rear reflected ring 43 to improve an accuracy of measurement. In one embodiment, the light structuring device 16 further includes a middle shutter 48. The shutter 47 and 48 are separately positioned between two mirrors. The number of shutter 48 can be set according to the number of the mirrors. Accordingly, the reflected rings 37, 38, 43 in the integrated image can be separated.

Figure 5:
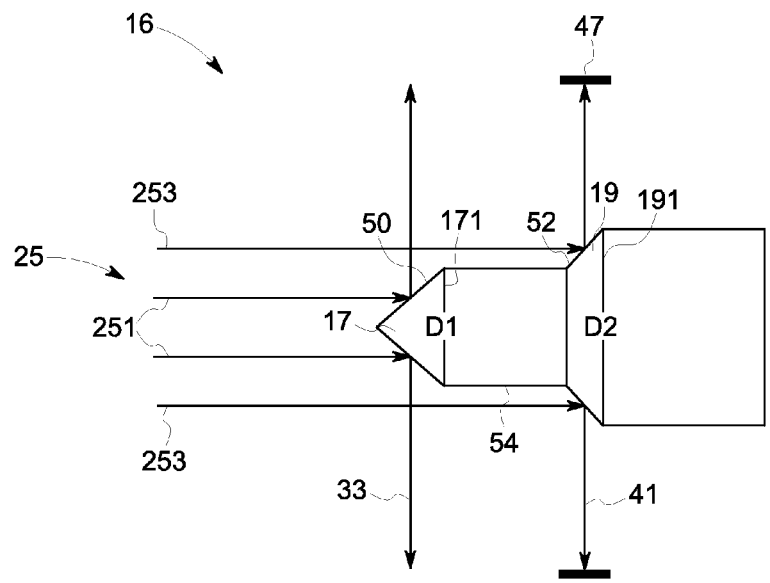
FIG. 5 is a schematic view of a light structuring device of the measuring system in accordance with another embodiment.

FIG. 5 illustrates a schematic view of the light structuring device 16 in accordance with yet another embodiment. A diameter D1 of a first bottom surface 171 of the front mirror 17 is less than that of the collimated light beam 25, and a diameter D2 of a second bottom surface 191 of the rear mirror 19 is larger than that of the first bottom surface of the front mirror 17. The front mirror 17 is smaller in diameter than the collimated light beam 25 and the rear mirror 19 is larger in diameter than the front mirror 17. Accordingly, the front conical reflecting surface 50 reflects the inner circle 251 of the collimated light beam 25 into the front focused ring of light 33, and the outer circle 253 of the collimated light beam 25 passes by the front mirror 17 to the rear mirror 19. The rear conical reflecting surface 52 of the rear mirror 19 reflects the outer circle 253 of the collimated light beam 25 into the rear focused ring of light 41.

In one embodiment, the front mirror 17 and the rear mirror 19 are integrally made as one piece. The front conical reflecting surface 50 and the rear conical reflecting surface 52 are arranged with a step 54 therebetween. The front conical reflecting surface 50 and the rear conical reflecting surface 52 are arranged apart from one another to make sure both conical reflecting surfaces 50, 52 receive the collimated light beam 25. In another embodiment, the front mirror 17 and the rear mirror 19 are made as separate pieces. For example, the front mirror 17 is a conical mirror smaller than the collimated light beam 25, and the rear mirror 19 is a conical mirror larger than the front mirror 17. The front mirror 17 and the rear mirror 19 in FIGS. 1, 3 and 4 may be formed as separate pieces. In the illustrated embodiment, the shutter 47 is positioned around the rear mirror 19, which may be a ring shutter to prevent the rear focused ring 41 from reaching the object.

Figure 6:
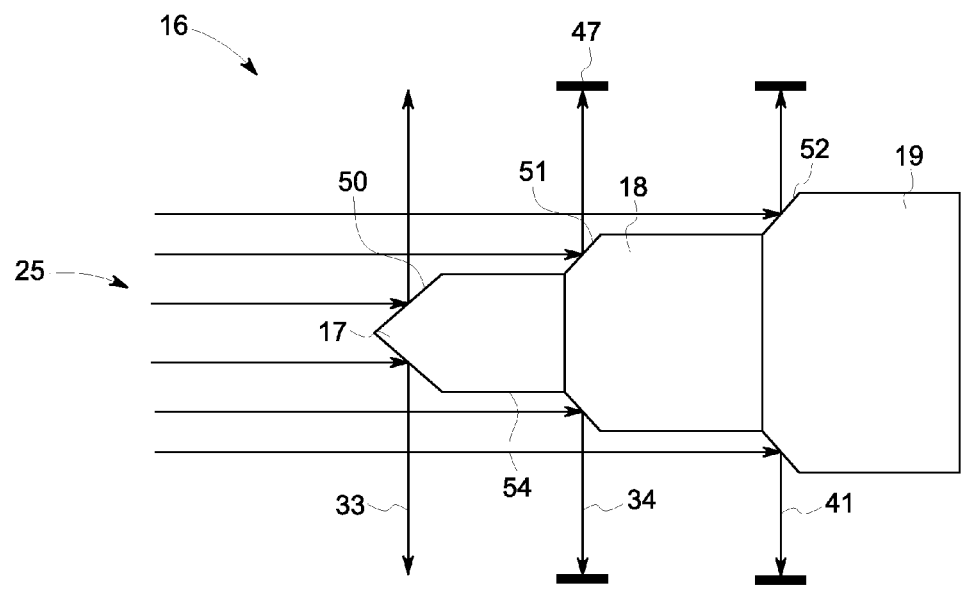
FIG. 6 is a schematic view of the light structuring device in accordance with another embodiment.

FIG. 6 illustrates a schematic view of the light structuring device 16 in accordance with another embodiment. The light structuring device 16 in FIG. 6 is similar to the light structuring device 16 in FIG. 5. Compared with the light structuring device 16 in FIG. 5, the light structuring device 16 includes a middle mirror 18 having a middle conical reflecting surface 51. The middle conical reflecting surface 51 reflects part of the collimated light beam 25 into a middle focused ring of light 34 and part of the collimated light beam 25 passes by the middle mirror 18 to reach the rear mirror 19. In another embodiment, two or more middle mirrors 18 are employed to form middle focused rings of light 34. The conical reflecting surfaces 50, 51 and 52 are arranged in one example apart from each other.

Figure 7:
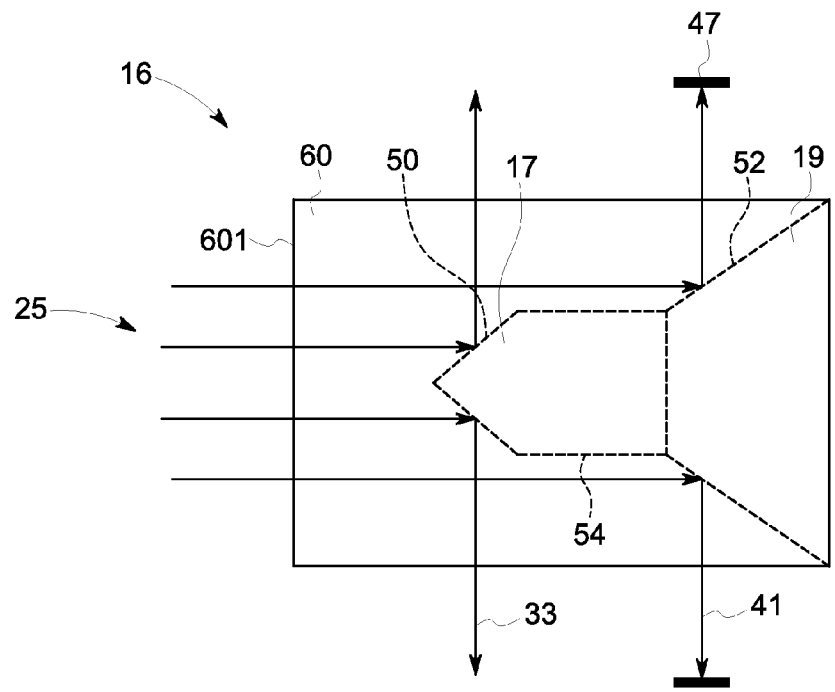
FIG. 7 is a schematic view of the light structuring device in accordance with another embodiment.

FIG. 7 illustrates a schematic view of the light structuring device 16 in accordance with another embodiment. The light structuring device 16 in FIG. 7 is similar to the light structuring device 16 in FIG. 5. Compared with the light structuring device 16 in FIG. 5, the front mirror 17 and the rear mirror 19 are integrally formed as an inner cone shape in one piece. The front mirror 17 and the rear mirror 19 are formed inside a piece of light-passing block 60 with a flat surface 601 which may be made from glass. The front conical reflecting surface 50 and the rear conical reflecting surface 52 are formed in an inner surface of the light-passing block 60 and made of reflective material to reflect collimated light beam 25. In one embodiment, the mirrors 17-19 of the light structuring device 16 in FIG. 6 may be formed as an inner conical prism which is similar to the light structuring device 16 in FIG. 7.

Figure 8:
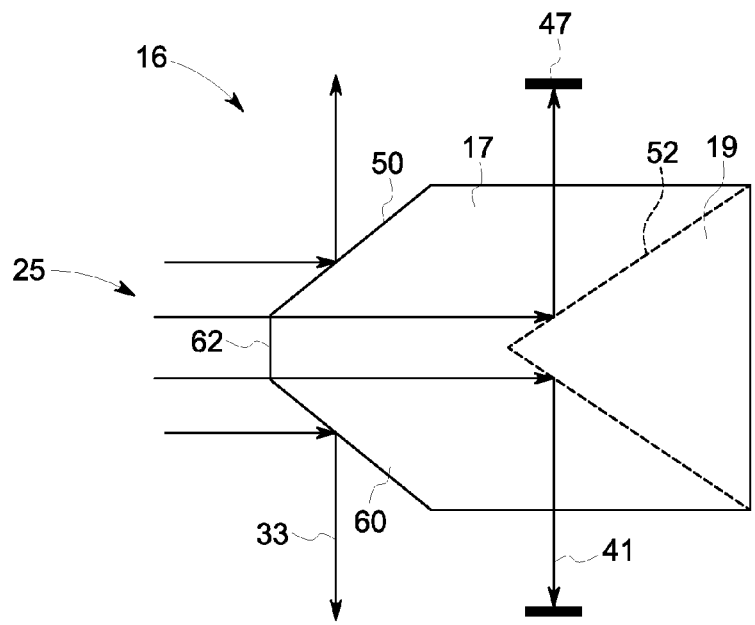
FIG. 8 is a schematic view of the light structuring device in accordance with another embodiment.

FIG. 8 illustrates a schematic view of the light structuring device 16 in accordance with another embodiment. The rear mirror 19 is formed as an inner cone shape inside the light-passing block 60. The front mirror 17 is formed on a front surface of the light-passing block 60. The apex of the front mirror 17 has a flat clear surface 62 to let part of the collimated light beam 25 pass by to the rear mirror 19. The reflecting surface 50 is formed on or added to the surface of the light-passing block 60.

Figure 9:
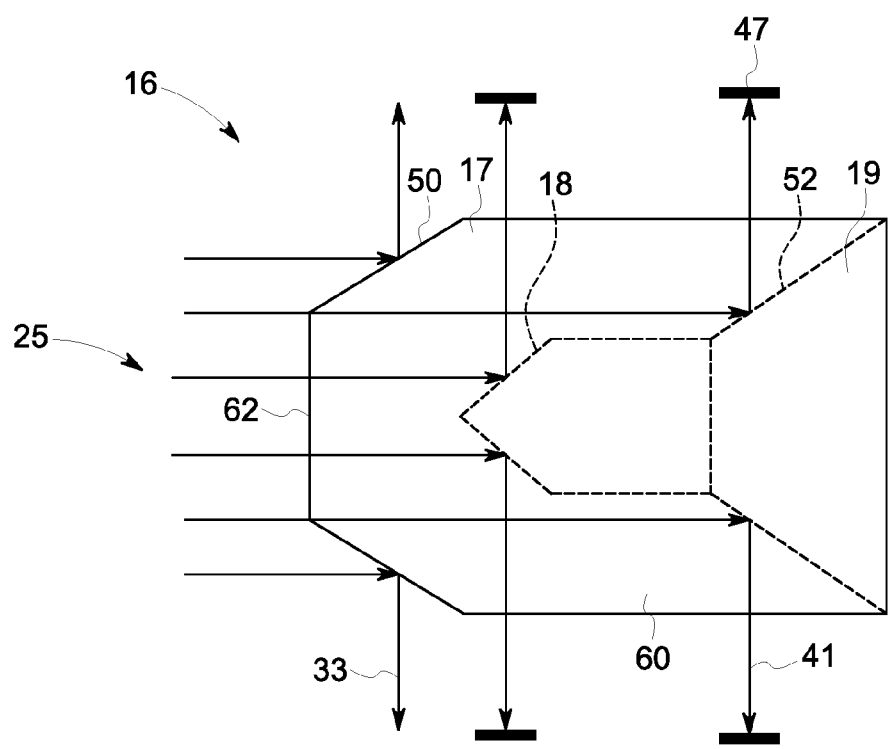
FIG. 9 is a schematic view of the light structuring device in accordance with another embodiment.

FIG. 9 illustrates a schematic view of the light structuring device 16 in accordance with another embodiment. The light structuring device 16 in FIG. 9 is similar to the light structuring device 16 in FIG. 8. Compared with the light structuring device 16 in FIG. 8, the light structuring device 16 in FIG. 9 further includes a middle mirror 18 formed inside the light-passing block 60. The middle mirror 18 is smaller than the rear mirror 19 to reflect part of the collimated light beam 25 and allows part of the collimated light beam 25 to pass by to the rear mirror 19. The middle mirror 18 and the rear mirror 19 have similar arrangements to the mirrors in FIGS. 5 and 7. In another embodiment, two or more middle mirrors 18 may be formed inside the light-passing block 60.

Figure 10:
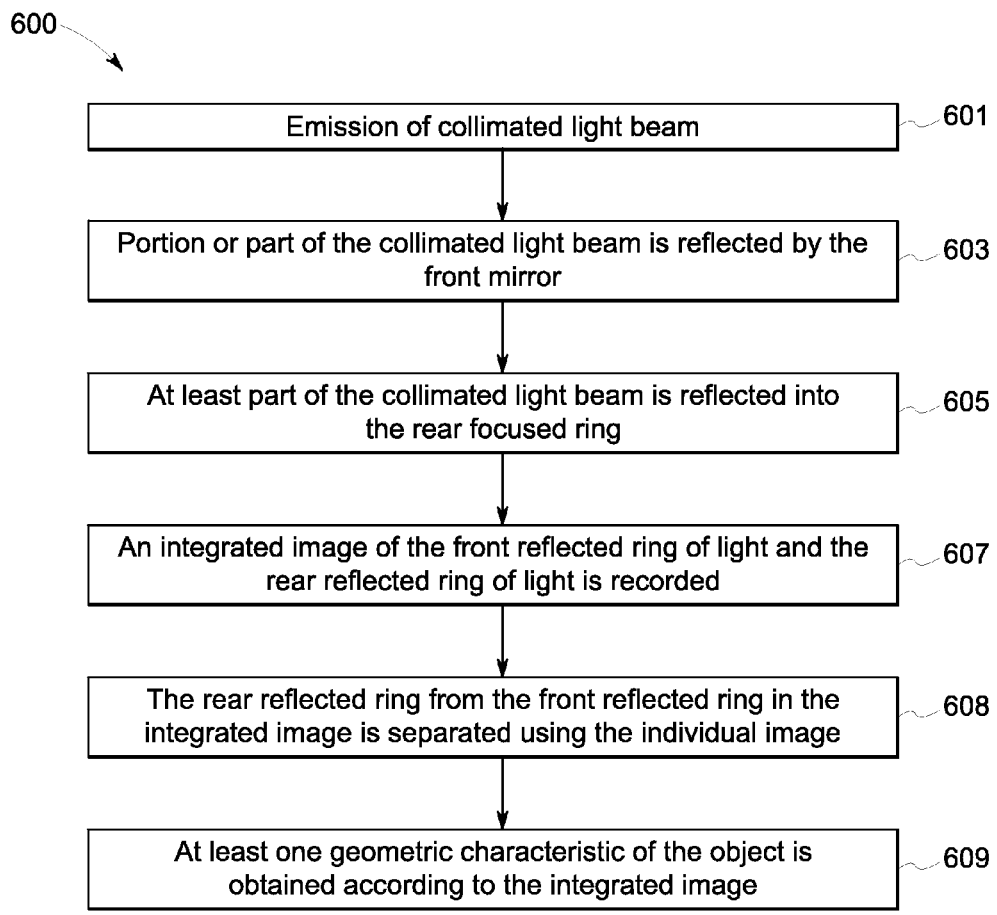
FIG. 10 is a flow chart of a method for measuring geometric characteristics of an object in accordance with an embodiment.

FIG. 10 illustrates a flow chart of a method 600 for measuring geometric characteristics of an object in accordance with one embodiment. A collimated light beam is emitted 601 such as from a light emitting unit. A portion or part of the collimated light beam is reflected by the front mirror 603 to reflect to produce and project a front focused ring of structured light to an object, in order to obtain a front reflected ring of light, wherein part of the collimated light beam passes by the front mirror. The collimated light beam is reflected into the front focused ring. The surface of the object reflects the front focused ring into the front reflected ring of light.

At least part of the collimated light beam that passes by the first mirror is reflected by the rear mirror to reflect and produce and project a rear focused ring of the structured light to the object to obtain a rear reflected ring of light and reflected into the rear focused ring 605. The surface of the object reflects the rear focused ring into the rear reflected ring of light. In one example the front plane of the front focused ring of the structured light is parallel to a rear plane of the rear focused ring of the structured light.

An integrated image of the front reflected ring of light and the rear reflected ring of light is recorded 607. The integrated image shows profiles of a front cross-section and a rear cross-section of a section of the surface of the object. At least one geometric characteristic of the object is obtained according to the integrated image 609. Corresponding points on the front reflected ring and the rear reflected ring are connected and processed to get the geometric characteristic of the object.

In one embodiment, an individual image of the front reflected ring is recorded and the rear reflected ring from the front reflected ring in the integrated image is separated using the individual image 608. In one example only the front reflected ring is imaged for the same section of the object so as to get the points on the front reflected ring. Accordingly, the points on the front reflected ring and on the rear reflected ring in the integrated image can be distinguished. In one example only the rear reflected ring is imaged for the same section of the object so as to get the points on the rear reflected ring. Accordingly, the points on the front reflected ring and on the rear reflected ring in the integrated image can be distinguished.

In one example the measurement device or the object is moved so that a further section of the object is imaged. By way of example, the measurement device can be housed in a borescope that is inserted into a pipe or cavity to obtain geometric characteristics of the object. The imaging can be used to look for cracks, warping, surface protrusions and the like.

Figure 11:
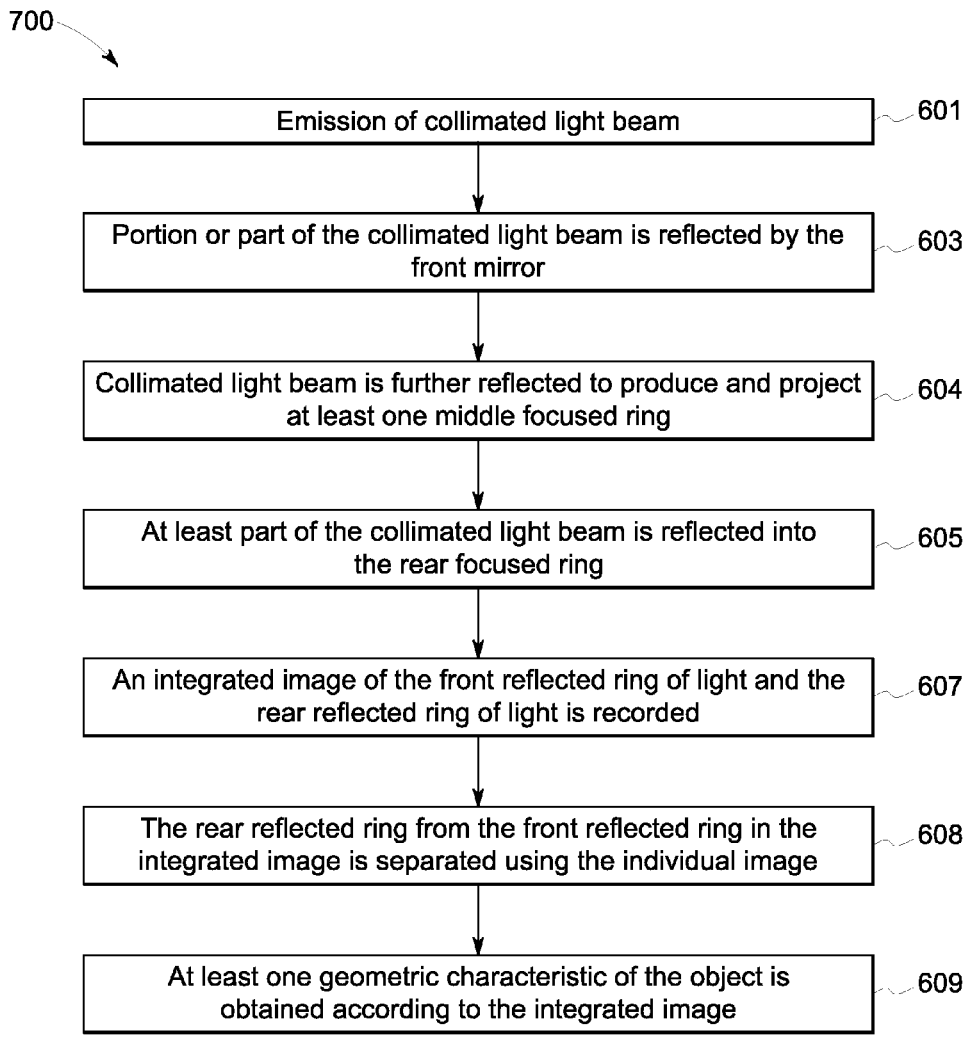
FIG. 11 is a flow chart of the method in accordance with another embodiment.

FIG. 11 illustrates a flow chart of a method 700 for measuring geometric characteristics of an object in accordance with another embodiment. The method 700 in FIG. 11 is similar to the method 600 in FIG. 10. Compared with the method 600 in FIG. 10, the method 700 in FIG. 11 further includes block 604. In block 640, the collimated light beam is further reflect to produce and project at least one middle focused ring of the structured light between the front focused ring and the rear focused ring to the object to obtain at least one middle reflected ring of light. The middle reflected ring of light is also imaged. The geometric characteristic of the object is obtained according to the image of the front reflected ring, the middle reflected ring and the rear reflected ring so as to improve an accuracy of measurement.

In order to distinguish the front reflected ring of light, the rear reflected ring of light and the one or more middle reflected rings of light according to one example, the rear and middle reflected rings of light are recorded separately and compared to the integrated image to separate the bands. In one example the front reflected ring and the middle reflected ring(s) are individually imaged for the same section of the object so as to get the points on the front reflected ring and middle reflected ring(s) respectively. Accordingly, the points on the front reflected ring, middle reflected ring(s) and the rear reflected ring in the integrated image can be distinguished. In one example the rear reflected ring and the middle reflected ring(s) are individually imaged for the same section of the object so as to get the points on the rear reflected ring and middle reflected ring(s) respectively. Accordingly, the points on the front reflected ring, middle reflected ring(s) and the rear reflected ring in the integrated image can be distinguished.

Figure 12:
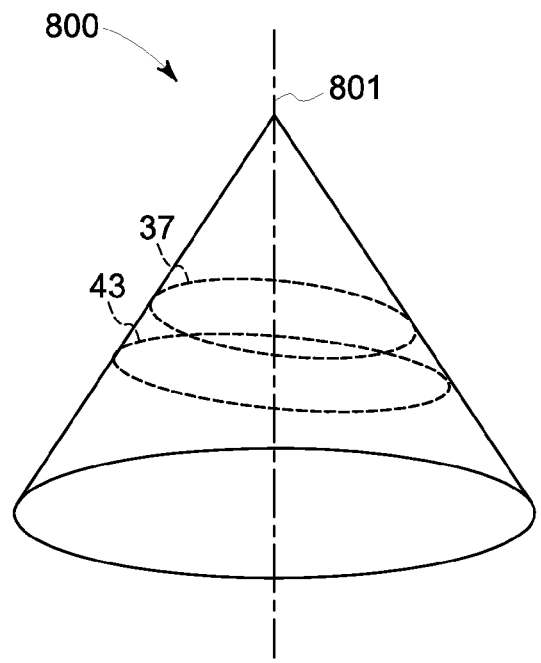
FIG. 12 is a perspective view of an object measured by the measuring system in accordance with an embodiment.

FIG. 12 illustrates a perspective view of a conic-shaped cavity object 800 measured by the measuring system 100, 300 or 400 in accordance with an embodiment. The measuring system 100, 300 or 400 obtains the front reflected ring of light 37 and the rear reflected ring of light 43 which are reflected from an inner face of the cone-shaped cavity. A 3D profile of the cone-shaped cavity is obtained through connecting corresponding points on the front reflected ring 37 and the rear reflected ring 43 so that the geometric characteristic of the object 800 is obtained. In this embodiment, the front reflected ring 37 and the rear reflected ring 43 are not vertical to a center axis 801 of the cone-shaped cavity.

Figure 13:
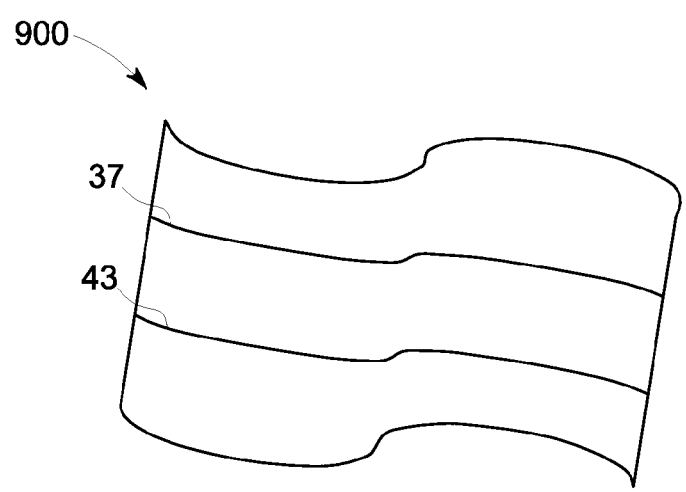
FIG. 13 is a perspective view of another object measured by the measuring system in accordance with another embodiment.

FIG. 13 illustrates a perspective view of an open curved surface object 900 measured by the measuring system 100, 300 or 400 in accordance with another embodiment. The measuring system 100, 300 or 400 obtains the front reflected ring of light 37 and the rear reflected ring of light 43 which are reflected from a surface of the open curved surface. The front reflected ring 37 and the rear reflected ring 43 each illustrate a curved line on the open curved surface, and a 3D profile of the open curved surface is obtained through connecting the corresponding points on the front reflected ring 37 and the rear reflected ring 43.

FIGS. 12 and 13 illustrate two embodiments of the object measured by the measuring system 100, 300 or 400, but not limited to these. The shape of the object between the front reflected ring 37 and the rear reflected ring 43 in one example has continuous linear change.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A system, comprising:
   a light emitting unit configured to emit a collimated light beam;
   a front mirror configured to reflect part of the collimated light beam to project front focused ring shaped structured light to an object to obtain a front reflected ring shaped light from the object, and wherein part of the collimated light beam is not reflected by the front mirror and passes by the front mirror;
   a rear mirror positioned downstream of a light transmitting path of the front mirror, the rear mirror configured to reflect at least part of the collimated light beam passing by, and not reflected by, the front mirror to project rear focused ring shaped structured light to the object to obtain a rear reflected ring shaped light from the object;
   an imaging unit configured to record an integrated image of the front reflected ring shaped light and the rear reflected ring shaped light together; and
   a processor coupled to the imaging unit and configured to obtain at least one geometric characteristic of the object according to the integrated image from the imaging unit.

2. The system of claim 1, wherein the front mirror comprises a light passing channel therein allowing the collimated light beam to pass by.

3. The system of claim 1, wherein a diameter of a first bottom surface of the front mirror is less than that of the collimated light beam, and a diameter of a second bottom surface of the rear mirror is larger than that of the first bottom surface of the front mirror.

4. The system of claim 1, wherein the front mirror comprises a front conical reflecting surface, the rear mirror comprises a rear conical reflecting surface, and the front conical reflecting surface and the rear conical reflecting surface are arranged with a space therebetween.

5. The system of claim 1, wherein the rear mirror is coaxial with the front mirror.

6. The system of claim 1, further comprising at least one middle mirror positioned in a light transmitting path between the front mirror and the rear mirror, the at least one middle mirror being configured to reflect part of the collimated light beam to project middle focused ring shaped structured light to the object to obtain middle reflected ring shaped light, and configured to pass by part of the collimated light beam to the rear mirror.

7. The system of claim 1, further comprising a shutter being operative to stop producing the rear reflected ring shaped light, and wherein the imaging unit is configured to record an individual image of the front reflected ring shaped light, and the processor is configured to separate the rear reflected ring shaped light from the front reflected ring shaped light in the integrated image using the individual image.

8. The system of claim 1, wherein the processor is configured to connect corresponding points on the front reflected ring and the rear reflected ring to obtain a three-dimensional profile.

9. A system, comprising:
a light emitting unit configured to emit a collimated light beam;
a light structuring device configured to generate structured light, comprising:
a front conical reflecting surface configured to reflect part of the collimated light beam into front focused ring shaped structured light to obtain front reflected ring shaped light, and wherein part of the collimated light beam is not reflected by the front conical reflecting surface and passes by the front conical reflecting surface; and
a rear conical reflecting surface configured to reflect at least part of the collimated light beam passing by, and not reflected by, the front conical reflecting surface into rear focused ring shaped structured light to obtain rear reflected ring shaped light;
an imaging unit configured to record an integrated image of the front reflected ring shaped light and the rear reflected ring shaped light together; and
a processor coupled to the imaging unit and configured to obtain the at least one geometric characteristic of an object according to the image from the imaging unit.

10. The system of claim 9, wherein the light structuring device comprises a light passing channel through the front conical reflecting surface to allow the collimated light beam to pass through.

11. The system of claim 9, wherein a diameter of a first bottom surface bounded by the front conical reflecting surface is less than that of the collimated light beam, and a diameter of a second bottom surface bounded by the rear conical reflecting surface is larger than that of the first bottom surface.

12. The system of claim 9, wherein the front conical reflecting surface and the rear conical reflecting surface are arranged with a step therebetween.

13. The system of claim 9, wherein the rear conical reflecting surface is coaxial with the front conical reflecting surface.

14. The system of claim 9, wherein the light structuring device further comprises at least one middle conical reflecting surface positioned in a light transmitting path between the front conical reflecting surface and the rear conical reflecting surface, the at least one middle conical reflecting surface is configured to reflect part of the collimated light beam into middle focused ring shaped structured light to obtain middle reflected ring shaped light, and configured to pass by part of the collimated light beam to the rear conical reflecting surface.

15. The system of claim 9, further comprising a shutter being operative to stop producing the rear reflected ring shaped light, and wherein the imaging unit is configured to record an individual image of the front reflected ring shaped light, and the processor is configured to separate the rear reflected ring shaped light from the front reflected ring shaped light in the integrated image with an assistance of the individual image.

16. The apparatus of claim 9, wherein the processor is configured to connect corresponding points on the front reflected ring and the rear reflected ring to obtain a three-dimensional profile.

17. A method, comprising:
emitting a collimated light beam;
reflecting part of the collimated light beam to produce and project a front focused ring shaped structured light to an object to obtain front reflected ring shaped light and passing a non-reflected part of the collimated light beam;
reflecting at least part of the passed collimated light beam to produce and project rear focused ring shaped structured light to the object to obtain rear reflected ring shaped light;
recording an integrated image of the front reflected ring shaped light and the rear reflected ring shaped light together; and
obtaining at least one geometric characteristic of the object according to the integrated image.

18. The method of claim 17, wherein a front plane of the front focused ring shaped structured light is parallel to a rear plane of the rear focused ring shaped structured light.

19. The method of claim 17, further comprising reflecting the collimated light beam to produce and project middle focused ring shaped structured light between the front focused ring shaped light and the rear focused ring shaped light to the object to obtain middle reflected ring shaped light.

20. The method of claim 17, further comprising recording an individual image of the front reflected ring shaped light and separating the rear reflected ring shaped light from the front reflected ring shaped light in the integrated image with an assistance of the individual image.

* * * * *